United States Patent [19]
Lange, III et al.

[11] Patent Number: 5,616,570
[45] Date of Patent: *Apr. 1, 1997

[54] USE OF NON-ABSORBABLE SYNTHETIC SULFATED POLYSACCHARIDES TO DECREASE CHOLESTEROL ABSORBTION

[76] Inventors: Louis G. Lange, III, 38 Kingsburg Pl., St. Louis, Mo. 63112; Curtis A. Spilburg, 2230 Willow Ridge La., Chesterfield, Mo. 63017

[*] Notice: The term of this patent shall not extend beyond the expiration date of Pat. No. 5,017,565.

[21] Appl. No.: 283,723

[22] Filed: Aug. 1, 1994

Related U.S. Application Data

[63] Continuation of Ser. No. 773,875, filed as PCT/US90/02079, Apr. 20, 1990, abandoned.

[51] Int. Cl.$^6$ ............................................. A61K 31/72
[52] U.S. Cl. ........................... 514/54; 514/55; 514/57; 514/59; 424/439; 426/658; 435/196
[58] Field of Search .................. 514/54, 55, 57, 514/59; 424/439; 426/658; 435/196

[56] References Cited

U.S. PATENT DOCUMENTS

| | | | |
|---|---|---|---|
| 3,511,910 | 5/1970 | Halleck | 514/54 |
| 3,627,872 | 12/1971 | Parkinson | 514/57 |
| 4,223,023 | 9/1980 | Furda | 514/55 |
| 4,436,731 | 3/1984 | Maltz | 536/20 |
| 4,623,539 | 11/1986 | Tunc | 514/56 |
| 5,017,565 | 5/1991 | Lange et al. | 514/54 |
| 5,063,210 | 11/1991 | Lange, III et al. | 514/54 |
| 5,484,777 | 1/1996 | Lange, III et al. | 514/54 |

FOREIGN PATENT DOCUMENTS

| | | |
|---|---|---|
| 2342782 | 9/1977 | France. |
| 49-43937 | 11/1974 | Japan. |
| 953626 | 3/1964 | United Kingdom. |
| 1164569 | 9/1969 | United Kingdom. |
| 1433732 | 4/1976 | United Kingdom. |

OTHER PUBLICATIONS

Bosner et al, Proc. Natl. Acad. Sci U.S.A, "Receptor–like Function of Haparin in the Binding and Uptake of Neutral Lipids", vol. 85, pp. 7438–7442, Oct. 1988.

Goto et al, J. Clin. Biochem. Nutr., "Effect of Dextran Sulfate (MDS) on Prevention of Ischemic Heart Disease Blind Primary Prevention Trail", 2: 55–70, 1987.

*Primary Examiner*—Chhaya D. Sayala
*Attorney, Agent, or Firm*—Banner & Allegretti, Ltd.

[57] ABSTRACT

This invention encompasses a method and compositions which inhibit pancreatic cholesterol esterase and triglyceride lipase and hence, lower cholesterol and triglycerides in the blood stream.

12 Claims, 10 Drawing Sheets

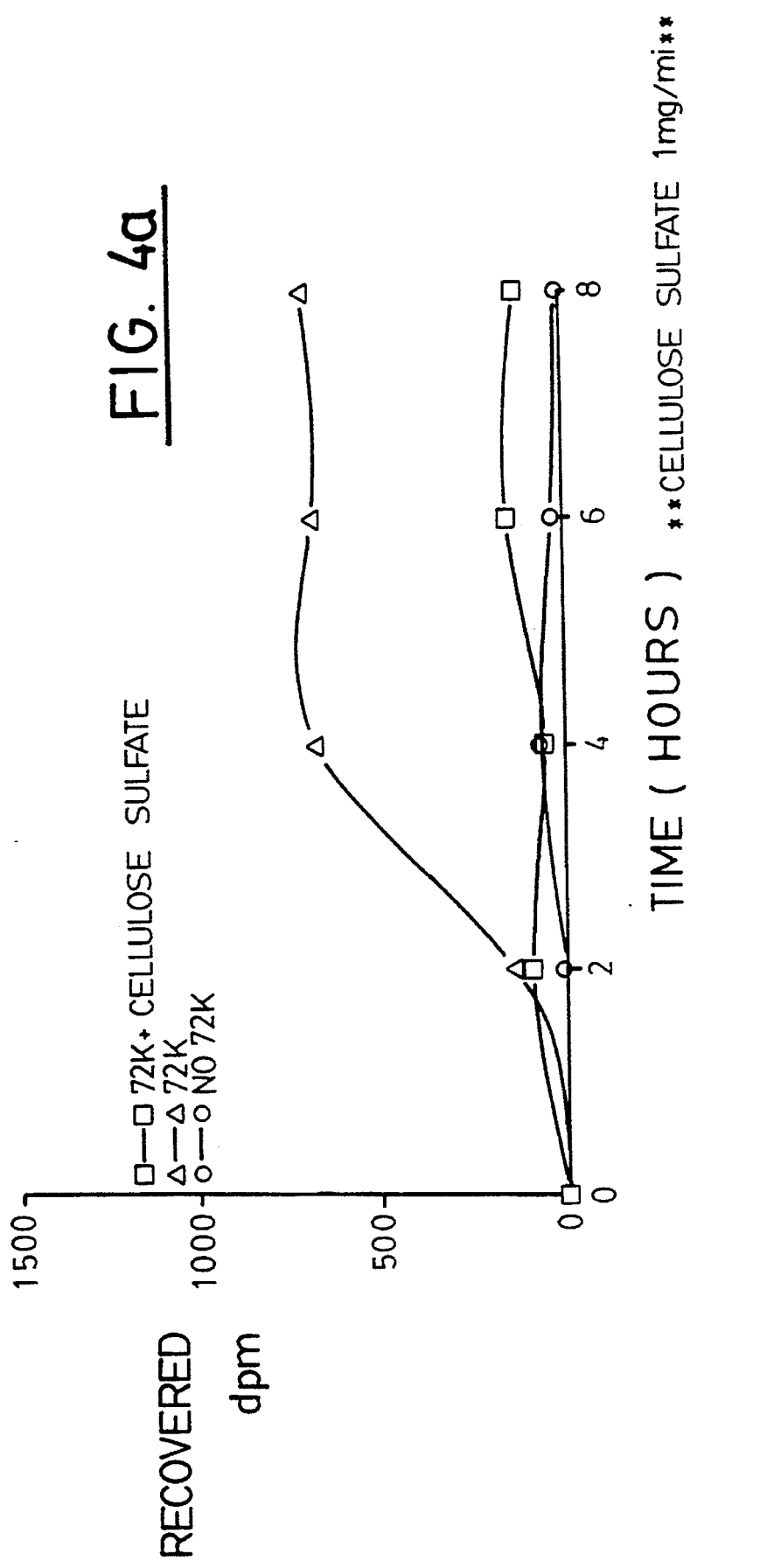

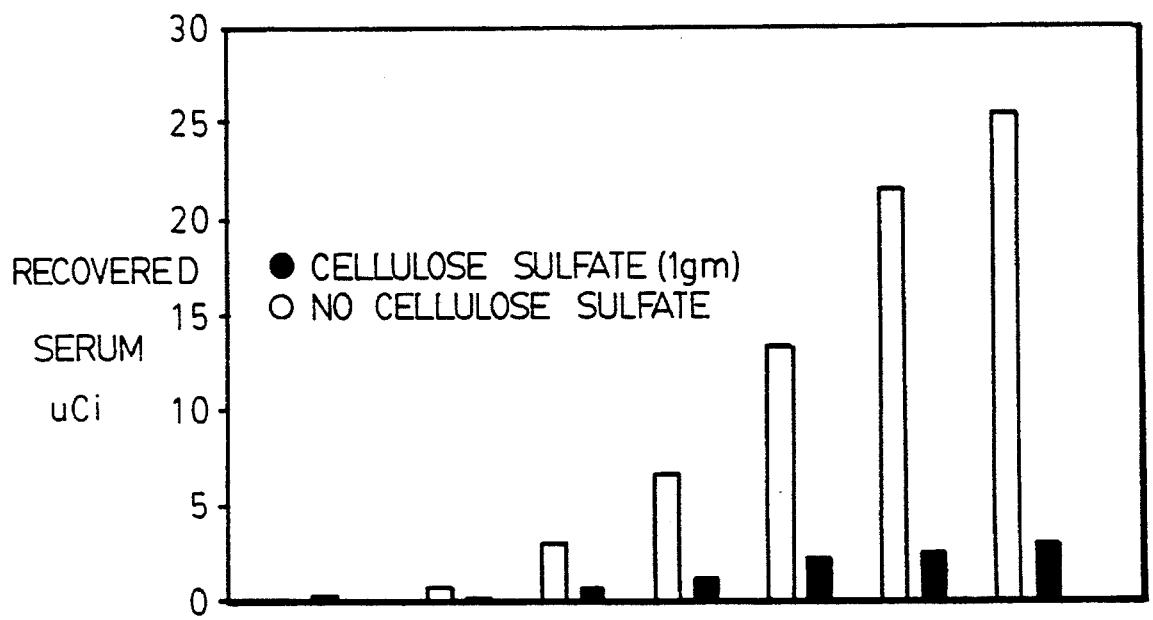
FIG. 5a
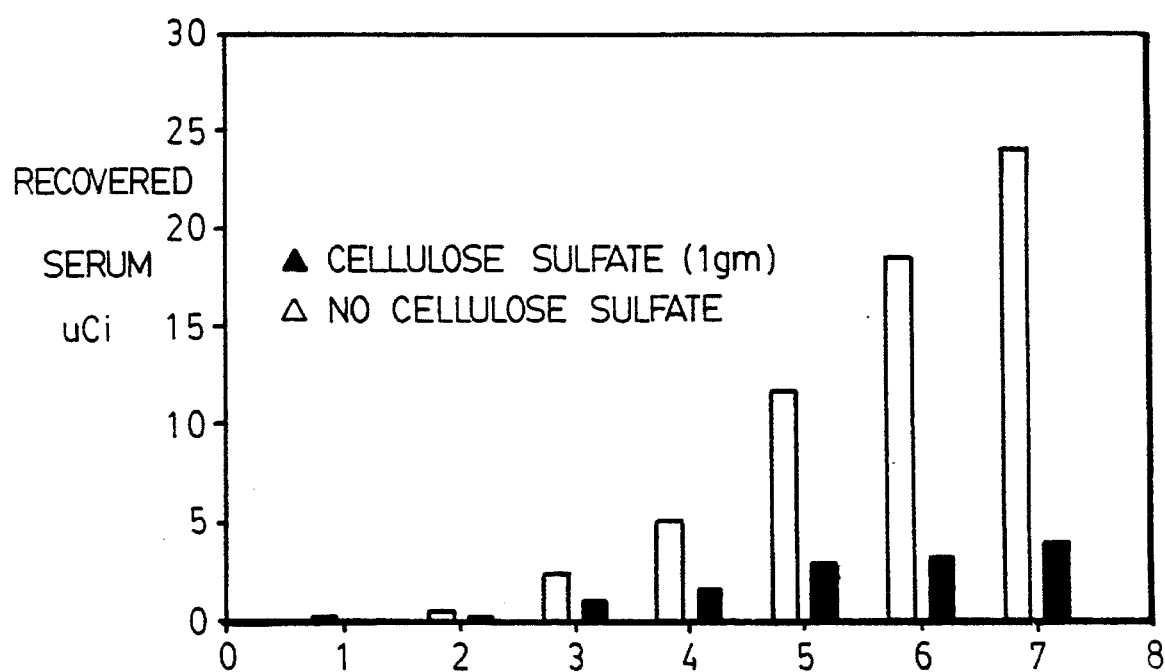
FIG. 5b   TIME (HOURS)

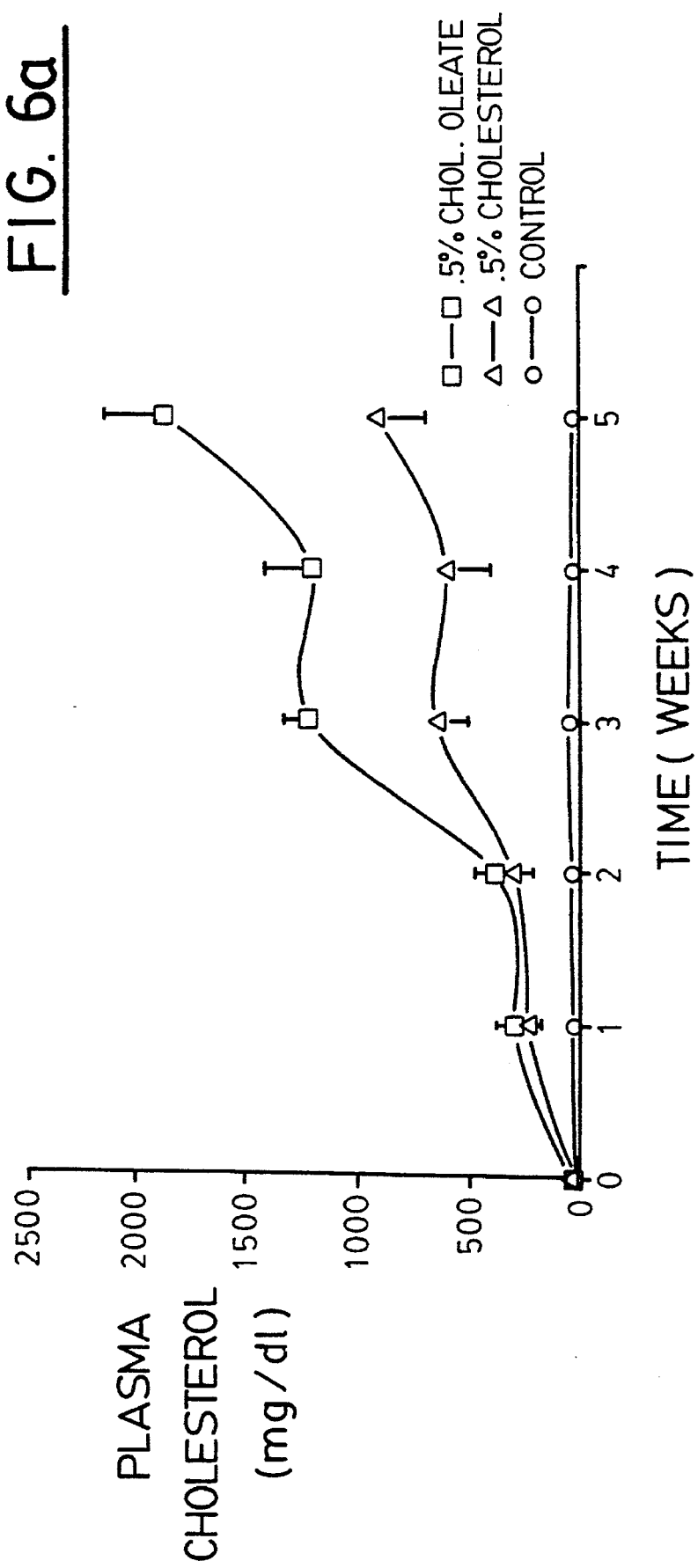

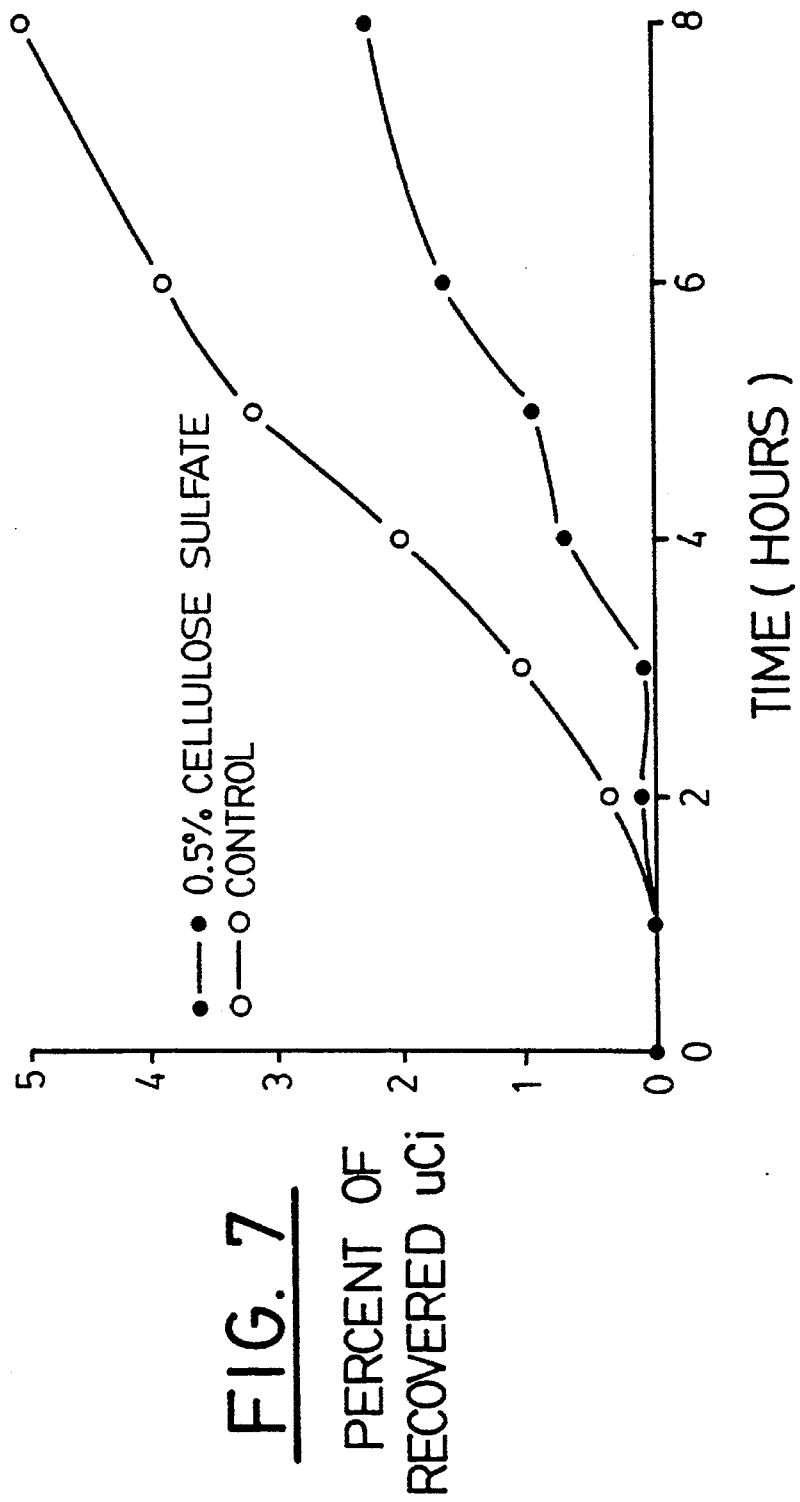
FIG. 7 PERCENT OF RECOVERED uCi
** DIET WAS MANTAINED FOR TWO DAYS

This application is a continuation of application Ser. No. 07/773,875, filed as PCT/US90/02079, Apr. 20, 1990, now abandoned.

USE OF NON-ABSORBABLE SYNTHETIC SULFATED POLYSACCHARIDES TO DECREASE CHOLESTEROL ABSORBTION

BACKGROUND OF THE INVENTION

This invention relates to a method for decreasing intestinal cholesterol absorption in man and, specifically to inhibiting or decreasing intestinal cholesterol and fatty acid absorption by oral administration of non-absorbable synthetic sulfated polysaccharides which inhibit the pancreatic cholesterol esterase catalyzed hydrolysis of naturally occurring and ingested cholesterol esters. The invention is based upon our discovery that cholesterol esterase is a more important contributor to overall dietary cholesterol absorption than previously accepted because of our surprising finding that (1) cholesterol derived from cholesterol esters is preferentially absorbed compared to free cholesterol and (2) cholesterol esterase enhances the absorption of free cholesterol. Thus, the surprising usefulness of inhibiting cholesterol esterase has demonstrated a new need for potent (Ki less than 5 µM) inhibitors of cholesterol esterase. The invention is based on our discovery and synthesis of non-absorbable, non-degradable sulfated polysaccharides which are potent inhibitors of human pancreatic cholesterol esterase, the enzyme responsible for promoting the intestinal absorption of cholesterol and fatty acids. This invention is also based on our observation that such agents are stable and bio-available to the intestine when delivered in baked goods such as biscuits and can therefore be administered in food products. This invention is also based upon our discovery that another class of potent non-absorbable inhibitors of cholesterol esterase are antibodies to cholesterol esterase.

Atherosclerosis is the leading cause of death in the United States and high serum cholesterol concentrations are associated with increased risks of fatal artherosclerotic events, JAMA, 1985, 253: 2094 (NIH Consensus Panel Report). In 1988, a Consensus Panel of experts at the NIH stated that a major public health priority was the reduction of cholesterol, and that the goal of front line therapy should be to diminish the intestinal absorption of cholesterol, either through eating less cholesterol or through the use of drugs which act in the intestine to reduce cholesterol levels, Arch. Int. Med., 1988, 148: 36 (Consensus Full Report). However, no mention was made of the importance of dietary cholesterol esters or attempts to lower cholesterol by inhibiting cholesterol esterase and no drugs now exist that block cholesterol absorption from the intestine. Currently, the principal drug to act within the intestine to lower cholesterol is cholestryamine, a bile acid sequestrant, "Agents to Treat Hyperlipidemia", The AMA Drug Evaluations, 6th Ed., p. 903. This agent binds bile salts within the intestinal lumen, and the resulting complex is excreted in the feces. Since bile acid is not re-absorbed, the liver uses additional cholesterol to synthesize more bile acid which effectively lowers the sterol concentration in the body. Bile salt sequestrants are effective in lowering cholesterol, but they seldom reduce cholesterol by more than 15%, and they are poorly tolerated by patients. Large quantities of these ion exchange resins must be ingested (15g or more), which lead to assaults on both the gustatory senses and intestinal function. Common side effects are constipation and bloating, JAMA, 1985, 253: 2095.

Cholesterol esterase is secreted by the pancreas after eating and is active in hydrolyzing ingested dietary esters of cholesterol. No role for it is established in the absorption of free cholesterol, but the enzyme has been regarded as essential for absorption of cholesterol derived from cholesterol esters. If enzyme activity is removed from pancreatic juice, no cholesterol absorption from cholesterol oleate occurs. If the cholesterol esterase activity is returned, absorption of cholesterol occurs, Borja et al., 1964, J. Physiol 206:223 and Vahouny and Treadwell, 1964, Proc. J. Exp. Biol. and Med. 116: 496. Since fatty acids that are absorbed come in part from cholesterol esters and they contribute to atherosclerosis, the enzyme cholesterol esterase may enhance atherosclerosis in two ways.

Despite this information and the stated mission of the NIH to target strategies of diminishing cholesterol absorption from the intestine, no study of pharmacological inhibition of human pancreatic cholesterol esterase has been performed. In fact, few studies have focused on the human enzyme at all, with most attention directed to other mammalian enzymes (rat, pig and cow) Calame et al., 1975, Arch. Biochem. Biophys. 168: 57; Van den Bosch et al., 1973, Biochem. Biophys. Acta 286: 94; Momsen et al., 1977, Biochem. Biophys. Acta 486: 103; Guy et al., 1981, Eur. J. Biochem. 117: 457; Slatton et al., 1986, Biochem. Biophys. Res. Comm. 134: 386; and Borgstrom, 1988, Biochem. Biophys. Acta 962: 308. Only one study has shown that a cholesterol esterase inhibitor can decrease cholesterol absorption in animals, Fernandez et al., 1989, Biochem. Biophys, Acta 1001: 249. However, this agent is a weak inhibitor of another activity of cholesterol esterase (Ki 100 µM), involving water soluble substrates and other reports claim that it does not inhibit cholesterol esterase at all, Hadvary et al., 1987, Int. J. Obesity 11: Suppl. 2, 21. In addition, this agent is 30% absorbed and metabolized. Thus, the lack of an appreciation of the importance of cholesterol esters in contributing to the overall absorption of cholesterol from the diet has prevented the development of inhibitors of cholesterol esterase, and no focus on non-absorbable inhibitors has been achieved.

Because of our discovery of the preferential absorption of these esters and the unexpected observation that cholesterol esterase can stimulate absorption of free cholesterol, there is now an important need to develop inhibitors of human pancreatic cholesterol esterase, especially those that are potent (Ki less than 5 µM), non-absorbable and non-degradable. The pharmacology of various sulfated polysaccharides has been investigated. Cook and Cammarata, 1963, Arch. Int. Pharmacodyn. 144: 1. In particular sulfated amylopectin has been taught in U.S. Pat. No. 4,150,110 as an anti-ulcer agent, but its properties as a cholesterol esterase inhibitor, which decrease absorption of cholesterol, have not been recognized. Sulfated dextran of low molecular weight has been recognized for use in the treatment of hyperlipemia and as an orally administered anticoagulant, British Patent No. 953,626. These sulfated dextrans, of low molecular weight (7000–8000, 7–8 kDa) developed for their enhanced absorption characteristics from the intestine, have been shown to reduce serum cholesterol levels at a dose of 1800 mg/day, Goro et al., 1987, J. Clin. Biochem. Nutr. 2: 55 by activating a blood enzyme, liproprotein lipase. However, their weak ability to inhibit cholesterol esterase or co-inhibit cholesterol absorption has not been recognized. They also have not been used as food additives. High molecular weight dextran sulfate has been excluded from development by others because of its lack of absorption and its attendant lack of activating serum lipoprotein lipase. Low molecular weight dextran sulfates because of their absorption cause changes in the integrity of the blood clotting system in man, a dangerous side effect in chronic usage, Drug In Japan (Ethical Drugs 10th ed. (1986) and see also product insert for MDS Kowa Tablet, Kowa Co., Nagoya Japan.

SUMMARY OF THE INVENTION

The present invention is directed to synthetic non-absorbable and non-degradable compounds and methods for decreasing intestinal absorption of cholesterol and fatty acid by inhibiting human pancreatic cholesterol esterase, now recognized by the present invention to be a key enzyme involved in mediating absorption, by orally administering synthetic non-absorbable sulfated polysaccharides in an amount effective for inhibiting pancreatic cholesterol esterase or by administering antibodies to cholesterol esterase.

BRIEF DESCRIPTION OF THE DRAWINGS

FIG. 5 shows the effect of cellulose sulfate on the cholesterol oleate fed rabbit.

FIG. 6a shows dietary effect of cholesterol and cholesteryl oleate.

FIG. 7 shows the effect of cellulose sulfate on serum cholesterol in the cholesterol ester fed rabbit.

DESCRIPTION OF THE PREFERRED EMBODIMENTS

Figure 1:
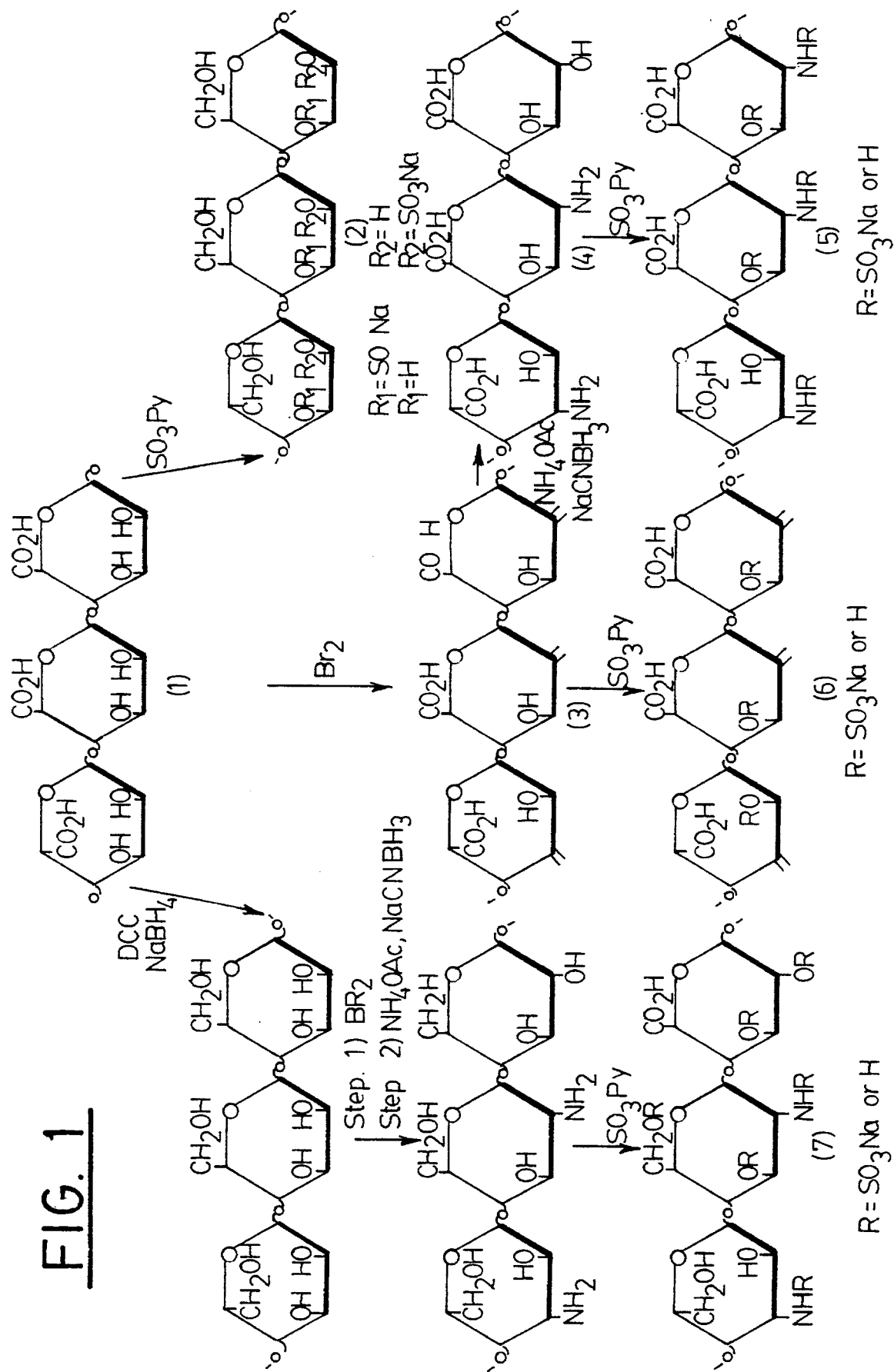
FIG. 1 shows the synthesis of various sulfated derivatives of alginic acid.

In accordance with the present invention, we have made certain discoveries concerning approaches to inhibiting cholesterol absorption from the intestine to reduce the level of serum cholesterol and tee incidence of atherosclerosis. Previously, a lack of understanding of the role that cholesterol esters play in the diet has precluded development of inhibitors of cholesterol esterase. Cholesterol esters have been thought to represent only 10 to 15% of total dietary cholesterol that is absorbed, Dietschy, Intestinal Lipid Absorption in Physioogy of the Gastrointestinal Tract, Vol. 2 p. 1170, 1981, Raven Press, N.Y. Because of the generally accepted thesis then that cholesterol esters are not very important, little attempt has been made to inhibit the intestinal absorption of cholesterol esters.

Our surprising discovery leading to a compelling need to develop inhibitors of cholesterol esterase is that the dietary contribution of cholesterol esters is very significant, approaching 45% in some foods. The reason for past misconceptions is that cholesterol esters are preferentially absorbed compared to free cholesterol, by more than 80%. In addition, other experiments indicate that cholesterol esterase also promotes the absorption of free cholesterol. These two new observations demonstrate that cholesterol esterase contributes significantly to total cholesterol absorption. Because of this surprising conclusion, there is an important need to develop inhibitors of human pancreatic cholesterol esterase. Thus, this previously ignored target for drug design is now important to investigate.

Apart from reactive chemical compounds used for non-specific covalent modification of protein groups which are unsuitable for in vivo use Lombardo et al., 1982, Biochemi. Biophys. Acta 67: 74, no inhibitors of human pancreatic cholesterol esterase have been reported. The ability of tetrahydrolipstatin to inhibit the rat pancreatic cholesterol esterase catalyzed hydrolysis of cholesterol esters has not been demonstrated. This agent is a potent inhibitor of the 52 kDa human pancreatic triglyceride lipage (Ki 0.1 μM) and it has been reported that it does not inhibit cholesterol esterase, Hogan et al., 1987, Int. J. Obesity II, Suppl. 3: 35–42 and Hadvary et al. 1987, Int. J. Obsesity II, Suppl. 2: 21. Other reports claim that this agent is a weak inhibitor of cholesterol esterase from rat (Ki 100 μM), Borgstrom 1988, Biochem. Biophys. Acta 962: 308. However, assays used in this work were conducted with water soluble artificial and colorimetric substrates instead of cholesterol esters. Since these are non-specific substrates, Worthington Enzyme Manual, Worthington Corp. Lilian Decker, ed. (1977), conclusions drawn are open to question. Other studies have also reported on inhibitors of pancreatic esterases using water soluble substrates, Ogawa et al. 1987, Chem. Pharm. Bull. 35: 4130; Ogawa et al., 1986 Chem. Pharm. Bull. 34: 1118; Ogawa et al., 1987, Chem. Pharm. Bull. 35 3276. No assay was conducted to demonstrate that inhibition of the hydrolysis of cholesterol oleate occurred. Their esterase substrates, methyl butyrate, N-acetyltyrosine ethyl ester and N-tosylarginine methyl ester are hydrolyzed by numerous pancreatic enzymes including trypsin and triglyceride lipase. Hence, no data demonstrate their ability to inhibit cholesterol esterase catalyzed hydrolysis of cholesterol esters. These agents are all small molecular weight and absorbed, Ogawa et al., 1986, Chem. Pharm. Bull. 34: 1118. Another report of a cholesterol esterase inhibitor also employed a water soluble substrate, Sutton et al. 1986 Biochem. Biophys. Res. Comm. 134: 386. Work in our laboratory has shown that the reported boronic acid derivative does not inhibit the cholesterol esterase catalyzed hydrolysis of cholesterol esters. In view of recent findings that triglyceride lipase has a separate active size for hydrolysis of water soluble substrates that is remote from the lipid hydrolyzing site, Winklet et al., 1990, Nature 343: 771, it cannot be understood that inhibitors of water soluble substrates teach about inhibition of cholesterol ester hydrolysis. Esterastin inhibits an intracellular form of cholesterol esterase, the lysosomal acid esterase but this enzyme is not the same as the secreted pancreatic enzyme and esterastin has not been recognized as an inhibitor of pancreatic cholesterol esterase Morin et al., 1989, Biochem. Biophys. Acta 1004: 139. A related study demonstrated that intra-gastric infusion of tetrahydrolipstatin at high concentrations (100 μM) not achievable by oral administration can significantly inhibit the cholesterol absorption in the rat when the source of cholesterol is cholesterol oleate. However, these workers did not observe inhibition of triglyceride lipase even though the concentration of the agent was 1000-fold above the Ki for lipase inhibition. This agent is also 30% absorbed and metabolized, Fernandez et al., 1989, Biochem. Biophys. Acta 1001: 249, leading to potential toxicity. Lastly, the results are in conflict with the lack of inhibition of cholesterol ester hydrolysis noted above in vito and thus this agent may work by a mechanism other than by enzyme inhibition.

Cholesterol esterase may be displaced from its binding site on the brush border membrane by heparin, Bosner et al., 1988, PNAS 85, 7438. Prior art teaches that orally administered heparin-like compounds that are naturally occurring such as Ateroid may decrease serum cholesterol by unknown mechanisms, Seethanathan et al., 1975, Mol. Cell. Biochem 8: 177. Heparin, being of low molecular weight varying from 10,000 to 20,000 is also taught as an absorbable agent, Folkman et al., 1983, Science 221: 719. Heparin which is naturally occurring like heparin sulfate, is expensive, costing $10,000 per kilogram and its binding interaction with cholesterol esterase is only $10^{-6}$ M. Another sulfated polysaccharide, chondroitan sulfate, which is naturally occurring, does not interact with cholesterol esterase, Bosner et al., 1988, PNAS 85, 7438. Lack of potency of the interaction of heparin with cholesterol esterase limits its use in man for chronic diseases since it is expensive and absorbed, with attendant side effects.

The present invention teaches non-obvious improvements over the prior art by demonstrating that synthetic polysaccharides with certain structural features which we define are (1) very potent inhibitors of cholesterol esterase, considerably more potent than are the naturally occurring compounds which we discovered inhibit the enzyme such as heparin (U.S. patent pending No. 168,424, filed 3/15/88), (2) non-absorbable from the intestine, (3) inexpensive (approximately $100/kg), and (4) more continuously in contact with the intestinal enzyme by virtue of (1) and (2). In accordance with the present invention, we have made certain discoveries concerning structural features of very large sulfated polysaccharide inhibitors (molecular weight greater than 100,000) of human pancreatic cholesterol esterase, which we have purified to homogeneity using cholesterol oleate hydrolytic activity as an assay. These include discoveries as to the synthesis and characteristics of sulfated polysaccharides that render highly specific derivatives with subnanomolar inhibitory constants. Many of these agents were prepared from non-mammalian and non-bacterial polysaccharides, which, along with their large size, makes them non absorbable and non-degradable, and thus with fewer side effects. Related agents of smaller size can be polymerized or bound to inert polymers to render them more effective. These agents are also specific for inhibiting the cholesterol esterase (100 kDA human pancreatic enzyme) catalyzed hydrolysis of naturally occurring cholesterol esters, such as cholesterol oleate, palmitate, linoleate, stearate and arachidonate. They do not inhibit human pancreatic triglyceride lipase (52 kDa). These agents can also displace human pancreatic cholesterol esterase from its binding site on the brush border membrane, Bosner et al., 1988, PNAS. 85,7438. Thus, these sulfated polysaccharides act to reduce cholesterol esterase facilitated absorption of cholesterol by at least two mechanisms-inhibiting enzymatic cleavage of cholesterol esters and displacing enzyme from its binding site on the intestinal cell. In addition, these agents, unlike tetrahydrolipstatin, do not cause steatorrhea in effective doses given to animals.

Moreover, our inhibitors of cholesterol esterase can be administered with inhibitors of triglyceride lipase. Since the bulk of fatty acid absorption occurs through the action of triglyceride lipase, its inhibition may lead to significant steatorrhea. Lower degrees of lipase inhibition can decrease fatty acid absorption, a progenitor of atherosclerosis, in combination with administration of cholesterol esterase inhibitors. Thus side effects can be minimized.

Persons having the skill in the art will recognize various triglyceride lipase inhibitors, such as, for example, tetrahydrolipstatin, which can be combined with the sulfated polysaccharide inhibitors of the present invention to reduce atherosclerosis.

Low molecular weight sulfated dextran (MDS-T) has been used to reduce serum cholesterol levels in Japan, Goro et al., 1987, J. Clin. Biochem. Nutr. 2: 55–70. The molecular weight of this bacterial dextran is between 7–8 kDa. This low molecular weight allows the sulfated dextran to be absorbed by the intestine as demonstrated by carbon-14 labelling studies (see product insert MDS Kowa, Injection and Tablet from the Kowa Company, Nagoya, Japan and see also Drugs In Japan (Ethical Drugs, 10th ed. 1986). It was developed for this property of intestinal absorption as indicated by the claim that faster decreases in serum lipids can be obtained by intravenous administration of this agent with clearance of serum lipemia due to activation of plasma lipoprotein lipase (see the same references). Clearly this route of administration will not lead to effects on inhibiting cholesterol esterase in the intestine. Absorption of MDS can lead to a variety of side effects, most notably, anticoagulant effects that must be monitored. This preparation has not been known to inhibit cholesterol esterase and it is sulfated in random and various ring positions.

Markedly increased inhibitory activities are realized from increased molecular weight of the polysaccharides and sulfation at a specific position; increased efficacy and decreased side effects are obtained by reducing absorption of the inhibitors. Increased displacement of cholesterol esterase from its binding sites on the brush border membrane is similarly achieved, Bosner et al., 1988, PNAS, 85,7438. Accordingly, the present invention includes non absorbable sulfated polysaccharides and those having a molecular weight greater than 20,000 (20 kDa) for use in inhibiting the activity of cholesterol esterase. The present invention is also directed to sulfated polysaccharides which are sulfated in a controlled manner at the 3-position.

Our investigations indicated that a variety of polysaccharide polymers that exist in nature can be sulfated to produce potent water soluble inhibitors of human pancreatic cholesterol esterase. Thus, we have reacted in a controlled manner in a variety of abundant, and cheap but water insoluble non-absorbable polysaccharides such as alginic acid (from seaweed, MW 240,000), pectin (from vegetable and fruit, MW 200,000), chitin and chitosan (MW 300,000 from mollusks), cellulose (from plants and trees, MW 500,000) and high molecular weight dextran (500,000MW from bacteria to produce sulfated derivatives, all with a molecular weight greater than 100,000. These derivatives are all non-absorbable from the intestine. They are also non-degradable by humans. Sulfation renders these polysaccharides water soluble, accessible to the enzyme and thus potent inhibitors of cholesterol esterase, whereas the parent starting materials are poorly water soluble and either not inhibitory or poorly inhibitory. In addition, sulfated amylopectin is an effective inhibitor of cholesterol esterase, a novel use not taught amongst its uses as a pharmaceutical agent described in U.S. Pat. Nos. 4,150,110 and 4,066,829. The use of dextran sulfate as a pharmaceutical agent is discussed in Am. J. Surgery, 1967, 13: 27. These disclosures are incorporated herein by reference.

Furthermore, agar, after extraction from algae and sulfation, is an extremely potent inhibitor of human pancreatic cholesterol esterase. Agar is a linear polysaccharide composed of alternating D-galactose and 3,6-anhydro-L-galactose units. Treatment of commercial gum agar results in a gel which is soluble in water. This aqueous solution inhibits human pancreatic cholesterol esterase with an IC50 of $3.3 \times 10^{-11}$ (MW=300,000). Native agar, in contrast, is a much weaker inhibitor of cholesterol esterase, having an IC50 of $3 \times 10^{-8}$. This inhibition may be due to the presence of agaropectin, a sulfated form of agar which is a minor contaminant of most commercial preparations of agar.

Not all sulfated polysaccharides inhibit cholesterol esterase. While a number of structural features can modulate the degree of inhibition, it is unexpected that the presence of a 3-sulfate markedly enhances inhibition and that not all polysaccharides inhibit cholesterol esterase, e.g., chondroitan sulfate which has its 3-position already occupied in the glycosidic bond. The presence of a 3-sulfate on the sugar ring is both necessary and sufficient for producing inhibitory activity in various polysaccharides toward human pancreatic cholesterol esterase. However, the presence of a 2-sulfate decreases inhibition while a 6-sulfate is unnecessary.

The efficacy of sulfated polysaccharides for decreasing absorption of cholesterol is increased by reducing the absorption of the polysaccharide from the intestine and thus prolonging its contact with the enzyme. High molecular weight sulfated polysaccharides are non-absorbable and, therefore, are necessary and sufficient to inhibit the absorption of cholesterol. The increased molecular weight also increases the inhibitory activity of the polysaccharides and sulfation increases solubility and access to enzyme to produce greater inhibition. For example, dextran sulfate of molecular weight 5000 (5 kDa) exhibited an IC50 of 20 nM while the IC50 of 500,000 molecular weight (500 kDa) dextran sulfate was 0.02 nM.

Accordingly, the present invention includes compounds of the formulas:

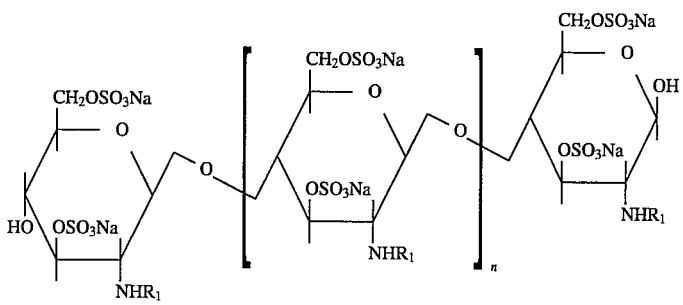

having a molecular weight greater than 20 kDA and wherein $R_1$ is —$COCH_3$ or —$SO_3Na$

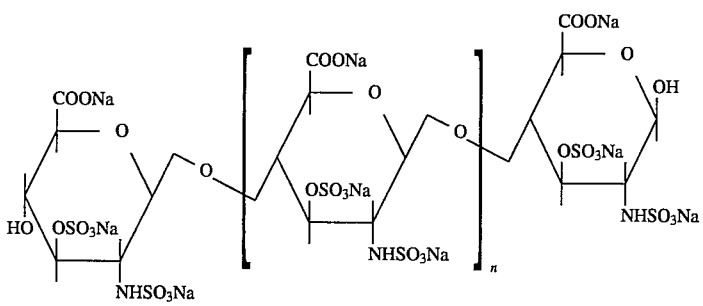

having a molecular weight greater than 20 kDa or

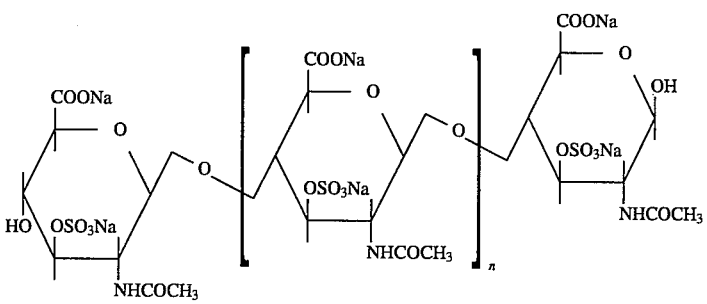

having a molecular weight greater than 20 kDa.

In essence, our discovery leads co a practical method for converting naturally occurring polysaccharide polymers often regarded as waste to a series of highly potent, cheap, non-absorbed and non-toxic and non-degradable inhibitors of cholesterol and fatty acid absorption that can be administered as a soluble agent in small and well-tolerated quantities. Those skilled in the art will recognize that methods to disperse and/or enhance or prolong the presence in the intestine of inhibitors to increase their contact with cholesterol esterase will further decrease the absorption of cholesterol.

These sulfated polysaccharides are also inhibitors of animal pancreatic cholesterol esterase. For example, cellulose sulfate inhibits the cholesterol esterase catalyzed hydrolysis of cholesterol oleate when the source of the enzyme is from the cow (Ki 0.1 μM), pig, rat or rabbit pancreas. Administration of cellulose sulfate to rabbits fed cholesterol oleate decreases cholesterol absorption by over 70%, while it also decreases absorption of free cholesterol as well.

These inhibitors can also be administered in combination with inhibitors of ACAT, fatty acyl cholesterol o-acyl transferase. These compounds can lower cholesterol but possess a number of toxic side effects since they are absorbed and not inert. Side effects can be lowered by reducing their dosage but maintaining efficacy in combination with inhibitors of cholesterol esterase that are not absorbed.

A person skilled in the art will recognize that various ACAT inhibitors, such as, for example, that described in Heider et al., 1983, J. Lipid Res. 24: 1127, which can be combined with the sulfated polysaccharides of the present invention to reduce serum levels of cholesterol.

These sulfated polysaccharide inhibitors of cholesterol esterase can be administered in pharmaceutical dosage forms such as tablets, capsules, liquids and powders. They can also be incorporated with food products such as biscuits and cookies. In essence, sulfated polysaccharides can be used as a dietary supplement to reduce cholesterol and fatty acid absorption, especially from foods rich in cholesterol esters where an unexpectedly large benefit would be obtained. Those skilled in the food and pharmaceutical arts will recognize a wide variety of formulations and vehicles for administering sulfated polysaccharides. Preferably, sulfated polysaccharides are administered with food or about the time of food intake and especially with foods that are rich in cholesterol esters. Moreover, these sulfated polysaccharide inhibitors of cholesterol esterase can be administered in combination with cholesterol synthesis blockers. Patients treated with cholesterol synthesis blockers experience various toxic side effects. This toxicity can be reduced by decreasing the dose of cholesterol synthesis blockers administered to the patient. Therefore, administering the sulfated polysaccharide of the present invention in combination with drugs that are absorbed by the intestine and block the endogenous synthesis of cholesterol allows for decreased dosages of cholesterol synthesis blockers to obtain the same end result. The toxicity associated with cholesterol synthesis blockers can be effectively reduced while still reducing serum cholesterol levels.

Persons having skill in the art will recognize various cholesterol synthesis blockers, such as, for example, lovastatin, which can be combined with the sulfated polysaccharides of the present invention to reduce serum levels of cholesterol.

A related class of sulfated, non-absorbable inhibitors of cholesterol esterase is a group of sulfated ion-exchange resins which are insoluble, such as mono-S (Pharmacia), Sephadex-SP (Sigma) and S-Sepharose (Pharmacia). These agents all bind tightly to cholesterol esterase and inhibit its function.

Another class of non-absorbable inhibitors of cholesterol esterase is antibodies raised against the enzyme and administered orally. These antibodies are stable at gastric pH and by binding to cholesterol esterase they produce a decrease in the amount of absorbed cholesterol by inhibiting the enzyme. A person skilled in the art will recognize that various methods of production of such antibodies exist, including various animals such as the cow that secrete antibodies in the milk and various cells that produce monoclonal antibodies. In addition, various formulations of such antibodies can be prepared to enhance their contact with cholesterol esterase in the intestine.

The invention is illustrated further by the following examples which are not to be construed as limiting the invention in scope or spirit to the specific procedures described in them.

EXAMPLE 1

Alginic acid from *Macrocystis pyrifera* (kelp) was dissolved in water at a concentration of 1 mg/ml. This stock solution was used to prepare various polysaccharide concentrations down to $10^{-5}$ mg/ml. Human pancreatic cholesterol esterase was purified as described by Bosner et al., *Proc. Nat'l, Acad, Sci.*, 85, 7438 (1988). To measure cholesterol esterase inhibition by alginic acid, 50 μl of cholesterol esterase (10 μg/ml), 75 μl of phosphatidylcholine vesicles containing cholesteryl $^{14}$C-oleate (1 mM 2,000 CPM/nmole), 25 μl of 100 mM taurocholate, 120 μl of 150 mM Tris, pH 7.5 and 30 μl of test alginic acid solution were incubated at 37° C. for fifteen minutes. The assay was quenched by placing the reaction vessels in a 4° C. ice bath and by adding 0.6 ml of 0.3 N NaOH and 3 ml of benzene/chloroform/methanol (1.0/1.2/0.5). The quenched reactions were vortexed for 30 seconds, centrifuged at 3,000 g for 15 minutes and 1 ml of the upper aqueous phase was added to 7 ml of Aquasol-2 (DuPont) with 0.025 ml of 6 N HCl. These mixtures were vortexed for one minute and counted for $^{14}$C-oleate. The counts were compared to a sample which contained cholesterol esterase but no alginic acid to determine the percentage of inhibition.

Following this assay procedure, alginic acid was tested for inhibition from $10^{-1}$ mg/ml to $10^{-4}$ mg/ml. As shown in Table 1, this polysaccharide had an $IC_{50}$ of 4 μg/ml or 20 nM (assuming a molecular weight 240 kDa).

EXAMPLE 2

Sulfation of alginic acid markedly enhances its inhibitory ability, as shown By preparing various sulfated derivatives (FIG. 1) and testing them as cholesterol esterase inhibitors.

Compound 2

Figure 2:
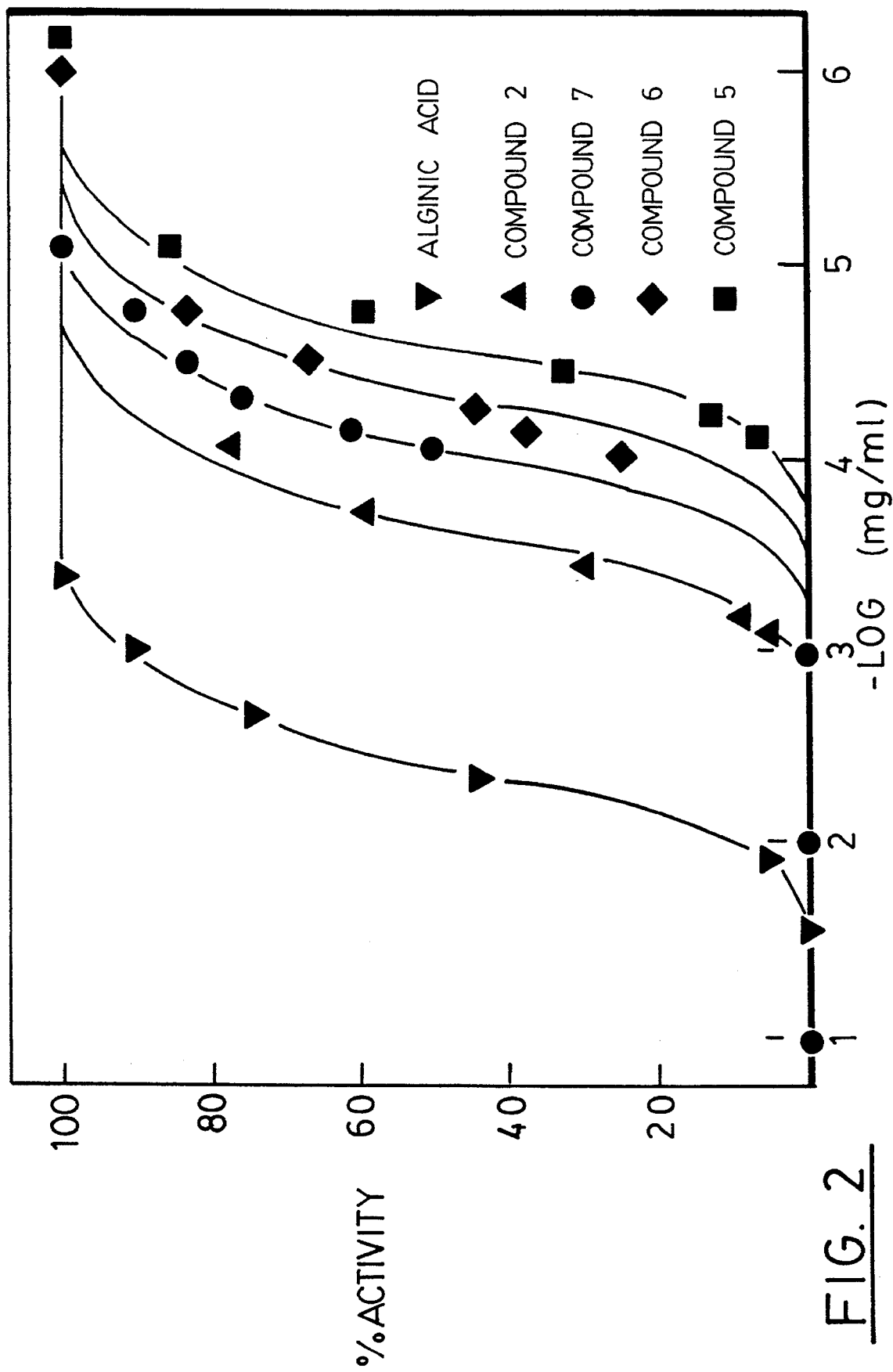
FIG. 2 shows the inhibition of cholesterol esterase by the various sulfated alginic acids.

Sodium alginate (150 mg) was treated with glacial acetic acid (5 cc) for two hours at room temperature, filtered and resuspended in N,N-dimethylformamide (5 ml). To the stirred solution, sulfur trioxide-pyridine Complex (1.5 g) was added over 30 minutes at room temperature and the resulting mixture was stirred overnight (16 hr). Dry pyridine (5 ml) was then added and the sulfated alginic acid was precipitated with 100 ml of acetone-methanol (9:1) mixture. The precipitate was dissolved in $H_2O$ (50 ml) and the pH of the solution was adjusted to pH8 with 1 N NaOH. Reprecipitation with acetone methanol (9:1) mixture (~200 ml) yielded the sodium salt of sulfated alginic acid. This compound was tested for cholesterol esterase inhibition as described above and it had an $IC_{50}$ of 0.25 μg/ml or 1.0 nM (Table 1 and FIG. 2).

Compound 5

Sodium alginate (1 g) was dissolved in 100 cc of deionized water, and 60 ml of 0.1 M bromine solution were added with stirring. The mixture was stirred at room temperature for 24 hr, and subsequently, the pH of the solution was adjusted to 8.0 with 1 N NaOH. After dialysis against water (6 liters×4) for 48 hours using 3,500 M.W. cut-off membrane, the solution was lyophilized to give 810 mg of oxidation product (Compound 3; Table 1).

To 575 mg of Compound 3 in water, 8 g of ammonium acetate and 8 g of sodium cyanoborohydride were added with stirring. The pH of the mixture was adjusted to 6.0 with O.1N HCl and stirring was continued at 40° C. for 48 hr. After cooling the mixture to room temperature, the pH of the solution was adjusted to 4.0 with 1 N HCl, and stirring was continued at room temperature for an additional 2 hrs. The reductive amination product was precipitated by adding absolute ethyl alcohol. This precipitate was dissolved in water (200 cc) and the pH was adjusted to 9 with 2 N NaOH solution. Treatment of this solution with 500 cc of ethyl alcohol-acetone (1:1) yielded a gelatin-type material which was collected by centrifugation. The resulting material was washed several times with absolute alcohol and acetone and lyophilized to yield 532 mg of the reduction product (Compound 4; Table 1).

Sulfation of Compound 4 was performed using sulfur trioxide-pyridine complex by the method described earlier (see Compound 2). This sulfated alginic acid (Compound 5; Table 1) was tested for cholesterol esterase inhibition, and it had an $IC_{50}$ of 0.025 μg/ml or 0.10 nM (Table 1 and FIG. 2).

Compound 6

Oxidized alginic acid (500 mg; Compound 3) was treated with glacial acetic acid (25 ml) for 2 hr, the residue was suspended in DMF (25 ml) and 5 g of sulfur trioxide-pyridine complex were added over 30 min while the DMF solution stirred at 4° C. The reaction mixture was allowed to warm to room temperature and it was stirred for an additional 24 hr. Pyridine (25 ml) was added to the reaction mixture and the sulfated product was precipitated by adding acetone:methanol (9:1) to the solvent mixture (500 cc). The residue was dissolved in 60 ml of water and it was converted to the sodium salt by adjusting the pH of the solution to 8 with 1N NaOH solution. The solution was dialyzed against water (4 liters×6) using 3,500 M.W. cut-off membrane over 48 hr and lyophilized to yield 520 mg of sulfated alginic acid (Compound 6; Table 1 and FIG. 2). This compound inhibited cholesterol esterase with an $IC_{50}$ of 0.06 µg/ml or 0.025 nM.

Compound 7

The sulfated alginic acid (Compound 7: Table 1) was prepared as described (Larm, O., Larsson, K., Scholander, E., Anderson, L. G., Holmes, E. and Soderstrom, G., 1979, *Carbohydrate Research* 73:332. This compound inhibited cholesterol esterase with an $IC_{50}$ of 0.10 µg/ml or 0.42 nM.

All the sulfated derivatives of alginic acid are superior inhibitors when compared to the native polysaccharide. These results are tabulated below and show that sulfation enhances inhibition from 20 to 200-fold:

TABLE 1

| Sample | $IC_{50}$(nM) | Enhancement Factor |
| --- | --- | --- |
| Alginic Acid | 20.0 | 1.0 |
| Compound 2 | 1.0 | 20.0 |
| Compound 5 | 0.10 | 200.0 |
| Compound 6 | 0.25 | 80.0 |
| Compound 7 | 0.42 | 48.0 |

EXAMPLE 3

Other common polysaccharides, when sulfated, also are potent inhibitors of cholesterol esterase.

Sulfated pectin was prepared by treating pectin (2 g) with glacial acetic acid, the polysaccharide was resuspended in dimethylformamide (25 ml), and the stirred suspension was cooled to 0° C. with an ice bath. Sulfur trioxide-pyridine complex (10 g, Aldrich) was added, and the temperature of the solution was allowed to reach room temperature. After stirring for an additional 3 hr, pyridine (20 ml) was added and the sulfated polysaccharide was precipitated with 95% ethyl alcohol (–300 ml). The precipitate was dissolved in water and the pH was adjusted to 7.5 with 1 N sodium hydroxide. Re-precipitation with 95% ethanol gave 1.8 g of the sodium salt of pectin sulfate. (Found: C. 34.53; H, 4.54; 0, 47.21; S, 0.77; Na, 8.31).

This compound was tested for cholesterol esterase inhibition and it had an $IC_{50}$ of 0.6 µg/ml or 3.0 nM (assuming a molecular weight of 200 kDa). Importantly, native, unsulfated pectin does not inhibit cholesterol esterase, demonstrating the importance of sulfation for effective inhibition.

Native pectin occurs naturally as the partial methyl ester of a(1→4) linked D-polygalacturonate sequences. The methyl ester was converted to the free acid by treatment with pectinesterase. Specifically, 1 g of pectin was dissolved in 100 ml of 0.1 M NACl. The pH was adjusted to 7.5 and pectinesterase (1.4 mg, 250 Units, Sigma) was added. The pH of the reaction mixture was maintained at 7.5 with 0.1 N sodium hydroxide solution. When there was no further change in pH, about 2 hr., the solution was transferred to dialysis tubing and dialyzed against water overnight (4 liters×4) Lyophilization of the dialyzed solution gave 820 mg of hydrolyzed pectin. The methyl ester cleaved product was sulfated in a similar manner as described above for native pectin. This sulfated pectin inhibited cholesterol esterase with an $IC_{50}$ of 0.04 µg/ml or 0.2 nM.

Chitin, another naturally occurring polysaccharide, also contains potential sites for sulfation. Thus, 300 mg of chitin were treated with 5 ml of glacial acetic acid for 2 hr. at room temperature, and The insoluble chitin collected and resuspended in 10 ml of DMF. Sulfur trioxide-pyridine complex (3 g) was added at room temperature and the reaction mixture was stirred. After 80 hr., 5 ml of pyridine were added and the solution stirred for an additional 30 min. Sulfated chitin was precipitated by adding 95% ethyl alcohol (100 ml), and The solid was suspended in 100 cc of water and the pH of the solution was adjusted to 7.5. The chitin solution was then dialyzed against water for 48 hr. The solution was filtered and the clear filtrate was lyophilized to yield 48 of sulfated chitin. Chitin sulfate inhibited human cholesterol esterase with an $IC_{50}$ of 0.3 nM (assuming a molecular weight of 300 kDa).

Since chitin is so insoluble, chitosan was used as starting material to increase the amount of sulfated material. Chitosan (1 g) was treated with 20 ml of glacial acetic acid for 2 hr at room temperature, and the residue was suspended in 25 ml of N,N-dimethyl formamide. To this stirred solution, sulfur trioxide-pyridine complex (10 g) was added at room temperature. The resulting mixture was stirred for 2 hr. and kept at room temperature for 72 hr. Pyridine (20 ml) was added and the sulfated chitosan was precipitated with acetone-methanol (9:1). It was then dissolved in 200 ml of water and the pH of the solution adjusted to 7.5 with 2 N sodium hydroxide solution. Re-precipitation with 95% ethyl alcohol gave the sodium salt of chitosan sulfate, which was redissolved in 200 ml of water. The polysaccharide solution was dialyzed against water (6 liters×4) for 48 hr and then lyophilized to give 1.12 of the sodium salt of chitosan sulfate. When tested as an inhibitor of cholesterol esterase, it gave an $IC_{50}$ of 0.3 nM.

Other commercially available, sulfated polysaccharides were also tested for inhibitory ability. Thus, cellulose sulfate (M.W.=500 kDa) had an $IC_{50}$ of 0.02 nM and dextran sulfate (M.W. 500,000) also had an $IC_{50}$ of 0.02 nM. Low molecular weight dextran sulfate (M.W. 5,000) had a markedly weakened Ki of 20 nM. The $IC_{50}$'s for all these sulfated compounds are summarized below in Table 2:

TABLE 2

| Compound | $IC_{50}$ (nM) |
| --- | --- |
| Pectin Sulfate | 3.0 |
| Pectin (Hydrolyzed) Sulfate | 0.2 |
| Chitin Sulfate | 0.16 |
| Chitosan Sulfate | 0.16 |
| Cellulose Sulfate | 0.02 |
| Dextran Sulfate[a] | 0.02 |
| Dextran Sulfate[b] | 20.0 |

[a]Dextran Sulfate of molecular weight 500,000
[b]Dextran Sulfate of molecular weight 5000.

In addition, amylopectin sulfate, prepared as described below, acts as an inhibitor of cholesterol esterase.

Into a jacketed reaction vessel equipped with means for mechanical agitation and containing 1,100 parts of softened water (deionized, distilled, or tap water may also be used) 275 parts of amylopectin fractionated from potato starch were added, with stirring. After 30 minutes agitation, the pH was adjusted to about 10.5–11.0 with portions of a 25%, by weight, aqueous NaOH solution. The temperature was 80° F.

Six hundred and twenty parts of a trimethylamine-sulfur trioxide complex were slowly added over a period of one and a half hours. Simultaneously, more of the 25% NaOH solution was introduced by means of a programmed addition designed to maintain the pH at 11.0. This programmed addition was maintained throughout the entire reaction.

After all the trimethylamine-sulfur trioxide addition product was added, the vessel was closed and a vacuum of 12" water was applied in order to initiate the removal of some of the trimethylamine which was being formed during the reaction. At the same time the temperature was slowly raised to 122° F. over a period of one and a half hours with continuing programmed additions of caustic. After 11 hours at 122° F., with caustic additions programmed to keep the pH at 11.0, the reaction was completed.

The vacuum was then raised to 27" mercury and the trimethylamine was removed by stripping while the pH was maintained at 11 through the programmed addition of the 25% NaOH solution. After the bulk of the trimethylamine was removed, water stripping was started using 1150 parts of water while keeping the pH at about 11.

The free trimethylamine content was reduced to below 100 p.p.m. after which the vacuum was removed and the solids adjusted to a level of 25%, by weight, and the pH to 10.8–11.0. The resulting solution was then dialyzed continuously against soft water, using parchment as a membrane to a salt content of 5% $Na_2SO_4$ based on the starch solids.

The pH at this stage was about 8. The product was then spray dried using an inlet temperature of 450° F., and an outlet temperature of 210° F.

The resulting spray dried amylopectin sulfate was in the form of a white powder and entirely devoid of any odor or taste resulting from the presence of any residual traces of unreacted trimethylamine.

EXAMPLE 4

The sulfated polysaccharides described here also inhibit the hydrolysis of triolein by the human 100 kDa cholesterol esterase. (The same assay procedure was used as described in Part I, only triolein was used instead of cholesteryl oleate.) As shown in the table below, the $IC_{50}$ for inhibition of triolein hydrolysis is nearly the same as that for cholesteryl oleate hydrolysis. These data indicate that these compounds are also useful agents for blocking the uptake of fats, as well as the uptake of cholesterol are summarized in Table 3.

TABLE 3

| Compound | Triolein | $IC_{50}$ (nM) Cholesteryl Oleate |
|---|---|---|
| Alginic Acid | 42.0 | 20.0 |
| Compound 2 | 3.3 | 1.0 |
| Compound 5 | 0.25 | 0.10 |
| Compound 6 | 0.83 | 0.25 |
| Compound 7 | 0.42 | 0.42 |
| Pectin Sulfate | 2.5 | 3.0 |
| Pectin (Hydrolyzed Sulfate) | 0.25 | 0.2 |
| Chitin Sulfate | 0.35 | 0.3 |
| Chitosan Sulfate | 0.85 | 0.3 |
| Cellulose Sulfate | 0.06 | 0.02 |
| Dextran Sulfate* | 0.08 | 0.02 |

*MW 500,000

EXAMPLE 5

The sulfated polysaccharides described here retain their inhibitory activity for prolonged periods at elevated temperatures. This property allows them to be stable under baking conditions and provides a convenient vehicle for their administration. For example, 109 mg of cellulose sulfate were added to 198 gm (7 oz) of corn muffin mix (Gold Medal,) and the solid ingredients were thoroughly mixed together. After the addition of one egg and one third cup milk, the muffin mix was stirred fifteen times. The mixture was poured into nine muffin tins and baked for fifteen minutes in a 400° oven. The next day one muffin was broken up, added to 100 ml of water and allowed to stand for fifteen minutes. The mixture was centrifuged and the clear supernatant was assayed for the presence of cholesterol esterase inhibition. The $IC_{50}$ of this solution was achieved when this solution was diluted $10^3$–$10^4$ times. These data indicate that the inhibitor is stable under baking conditions and that it can be released into solution from baked goods.

EXAMPLE 6

Sulfated agar was prepared from commercial agar by first suspending 2 g of Commercial agar in N, N-dimethylformamide (25 ml), and cooling the stirred suspension to 0° C. with an ice bath. Sulfur trioxide-pyridine complex (10 g, Aldrich) was added, and the temperature of the solution was allowed to reach room temperature. After stirring for an additional 3 hr, pyridine (20 ml) was added and the sulfated polysaccharide was precipitated with 95% ethyl alcohol (~300 ml). The precipitate was dissolved in water and the pH was adjusted to 7.5 with 1 N sodium hydroxide. Reprecipitation with 95% ethyl alcohol gave sulfated agar.

Human pancreatic cholesterol esterase was purified as described by Bosner et al., Proc, Natl. Acad. Sci,, 85, 7438 (1988). To measure pancreatic cholesterol esterase inhibition by sulfated agar, 50 µl of pancreatic cholesterol esterase (10 µg/ml), 75 µl of phosphatidylcholine vesicles containing cholesteryl $^{14}$C-oleate (1 mM 2,000 CPM/nmole), 25 µl of 100 mM taurocholate, 120 µl of 150 mM Tris, pH 7.5 and 30 µl of test sulfated agar solution were incubated at 37° C. for fifteen minutes. The assay was quenched by placing the reaction vessels in a 4° C. ice bath and by adding 0.6 ml of 0.3 N NaOH and 3 ml of benzene/chloroform/methanol (1.0/1.2/0.5). The quenched reactions were vortexed for 30 seconds, centrifuged at 3,000 g for 15 minutes and 1 ml of the upper aqueous phase was added to 7 ml of Aquasol-2 (DuPont) with 0.025 ml of 6 N HCl. These mixtures were vortexed for one minute and counted for $^{14}$C-oleate. The counts were compared to a sample which contained cholesterol esterase but no sulfated agar to determine the percentage of inhibition.

Following this assay procedure, sulfated agar was determined to have an $IC_{50}$ toward human pancreatic cholesterol esterase of $3.3 \times 10^{-11}$ M, or 0.033 1 nM (based on a molecular weight of 300 kDa).

The $IC_{50}$ was determined for native (unsulfated) agar to be $3 \times 10^{-8}$ M, or 30 nM. This inhibition may be due to minor (<0.1%) contamination of agar by agaropectin, a sulfated form of agar found in most commercial preparations of agar.

EXAMPLE 7

Figure 3:
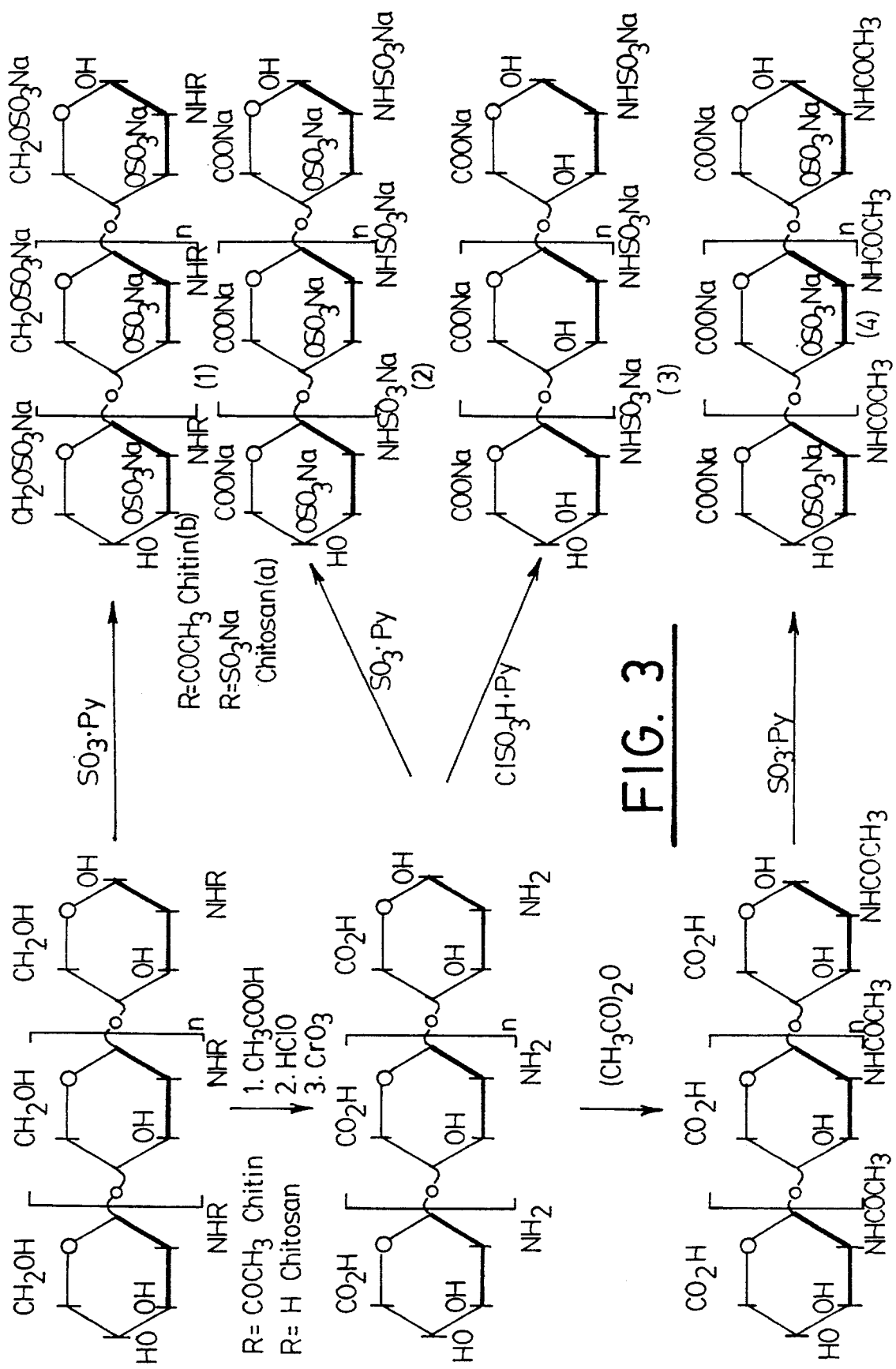
FIG. 3 shows the synthesis of chitosan sulfated at various and specific ring positions.

The structural basis for the potent inhibition of human pancreatic cholesterol esterase exhibited by chitosan (0.3 nM. Example III) was determined by preparing a number of chitosan derivatives sulfated at various positions on the polysaccharide ring (FIG. 3). Five different compounds were synthesized using the strategy outlined in Table 4, and their inhibitory activity was determined in the assay described in Example 6, above. The structure activity relationships for the five sulfated polysaccharides is summarized below.

As the data demonstrates, the presence of 3-sulfate is both necessary and sufficient to produce inhibitory activity by these polysaccharides toward human pancreatic cholesterol esterase. However, sulfation at the 2-position decrease activity while 6 sulfation is unnecessary.

TABLE 4

| COMPOUND | SULFATION POSITION | | | IC$_{50}$ nM |
|---|---|---|---|---|
| | 2[a] | 3[b] | 6[b] | |
| Ia | + | + | + | 0.3 |
| Ib | − | + | + | 0.3 |
| II | + | + | − | 1.6 |
| III | + | − | − | N.I. |
| IV | − | + | − | 0.3 |

[a] Position 2 is N-sulfation;
[b] positions 3 & 6 are 0-sulfation.
N.I. - Not Inhibitory

EXAMPLE 8

Figure 4B:
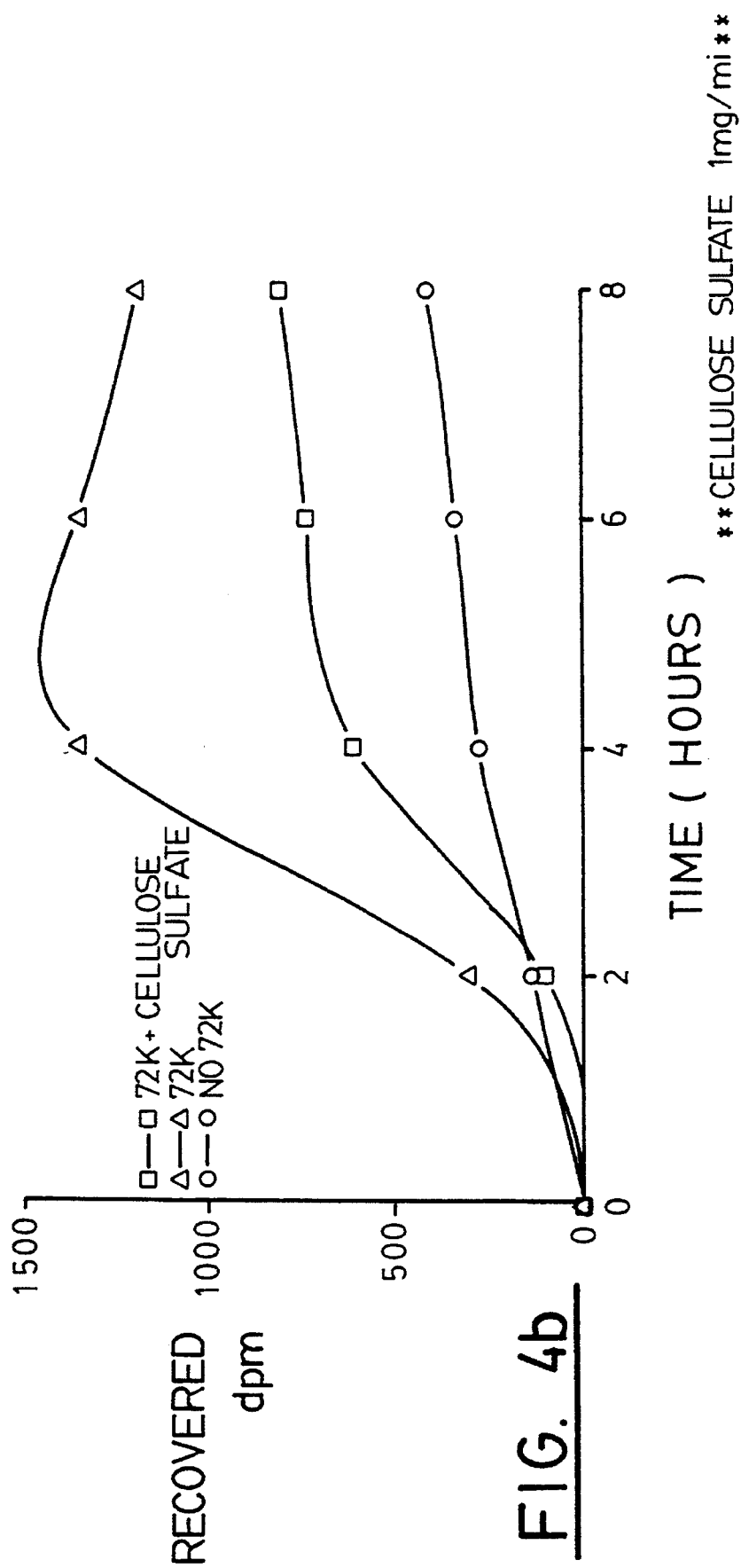
FIG. 4a and b shows the inhibition by cellulose sulfate of cellular uptake of esterified and free cholesterol, respectively.

Colonic adenocarcinoma cells (CaCo-2, American Type Culture Collection) were grown to a density of 2×10$^6$ cells on 25 mM coverslips in Dulbecco's Moditied Eagle's Medium containing 10% (v/v) lipoprotein depleted serum. The coverslips were washed with phosphate buffered saline (PBS) and transferred to 35 mm wells containing 1.0 ml PBS, 2 mM taurocholate and 1% bovine serum albumin. The cells were then incubated at 37° C. with 0.01 uCi of $^3$H cholesterol and 0.01 uCi of $^{14}$C-cholesteryl oleate, which were embedded in phosphatidylcholine vesicles. The control wells received no cholesterol esterase while the experimental set received bovine 72 kDa cholesterol esterase. At various incubation times the coverslips were removed, washed three times with PBS, and the cells were collected by scraping and washing with 250 mM tris glycine buffer (pH 8.8) containing 0.1% SDS. The cells were collected by centrifugation and the pellet was heated at 100° C. for five minutes and then sonicated for ten minutes. The uptake of cholesterol, either from free sterol or from cholesteryl oleate, was determined by scintillation counting for $^3$H or $^{14}$C, respectively. As shown in FIG. 4, cholesterol esterase catalyzed the uptake of cholesterol derived from cholesteryl oleate (FIG. 4a), and it also catalyzed the uptake of free cholesterol (FIG. 4b). In both instances, cellulose sulfate markedly inhibits cholesterol uptake by the cells (FIG. 4a and b, squares).

EXAMPLE 9

Inhibition of cholesterol uptake from either free cholesterol or from cholesteryl oleate was examined in vivo using cellulose sulfate. A rabbit which had been fed cholesteryl oleate for six weeks was fasted for twelve hours and a nasogastric cube was inserted into its stomach. Five ml of a cellulose sulfate solution (100 mg/ml) in Tris buffer were added followed by 10 ml of 20 uCi of $^3$H cholesterol incorporated in phosphatidylcholine vesicles and 10 ml of 20 uCi of $^{14}$C cholesteryl oleate. The nasogastric tube was then flushed with an additional 5 ml of cellulose sulfate solution (100 mg/ml). After the tube was removed, blood was drawn from an ear vein as a function of time and 100 µl of plasma was counted for $^{14}$C and $^3$H. As shown, cellulose sulfate inhibited by 85% the uptake of either free cholesterol or cholesterol derived from cholesteryl oleate (FIG. 5).

EXAMPLE 10

Figure 6B:
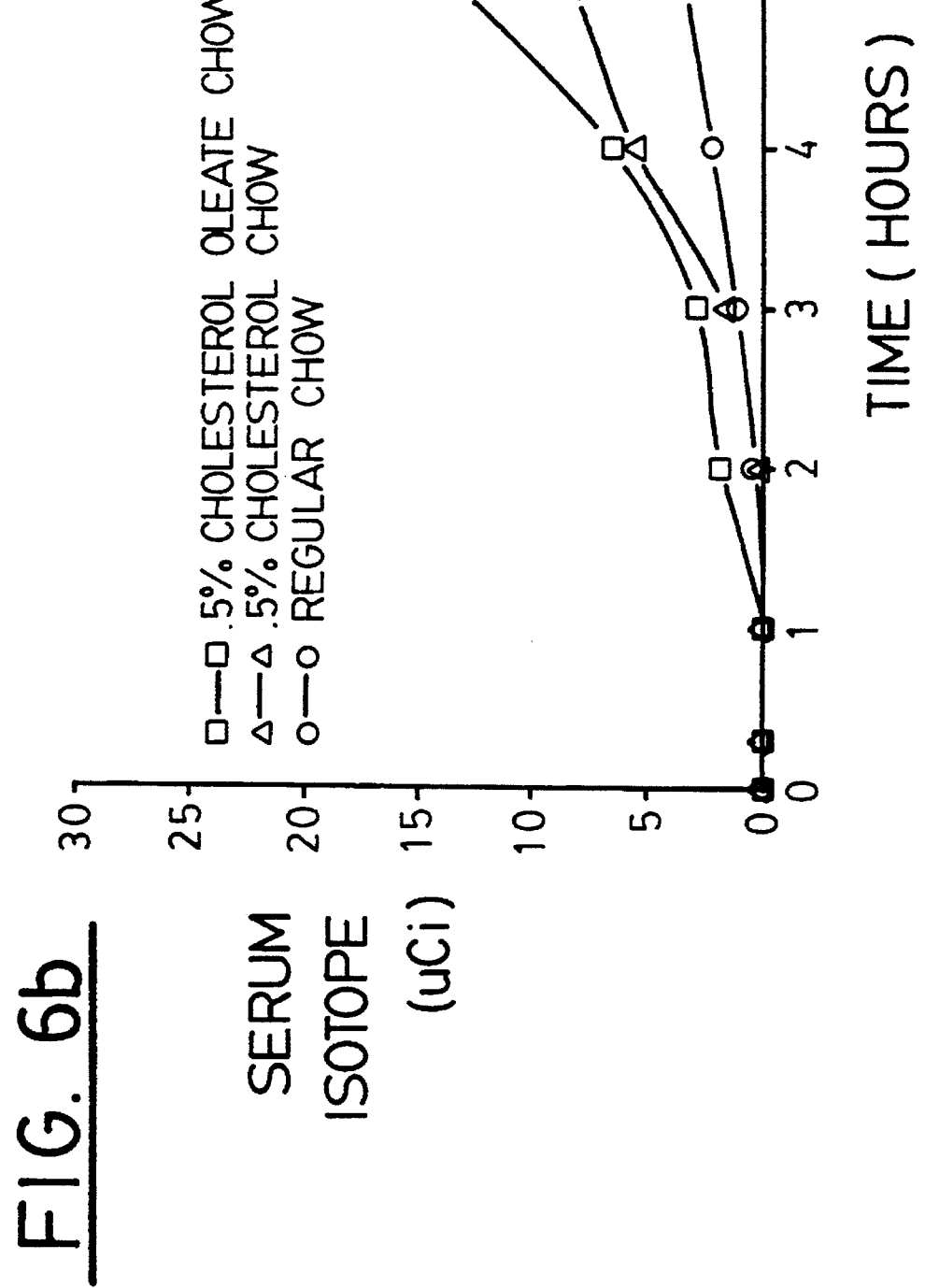
FIG. 6b shows serum recovery of $C_{14}$ cholesterol from labeled cholesterol oleate chow and cholesterol chow.

Nine New Zealand White rabbits (2–2.5 kg) were maintained on regular rabbit chow and their serum cholesterol was found to vary from 21 to 66 mg/dl when measured using the enzymatic colorometric method (Wako Pure Chemical Industries, Limited). The rabbits were then split into three groups of three each. One group was fed regular chow, the second group was fed cholesterol chow (5 gm/kg, 0.5% in sterol) and the third was fed cholesteryl oleate chow (8.66 gm/kg, 0.5% in sterol). At one week intervals, blood (1.0–1.5 ml) was drawn from an ear vein and the serum cholesterol in 10 microliter samples was determined in duplicate. As shown in FIG. 6a, rabbits on regular chow showed no change in serum cholesterol over the five week experimental period. On the other hand, the cholesterol fed rabbits experienced a 35-fold increase in their serum cholesterol level over the same time period. This increase was even more marked (70-fold) in those rabbits fed cholesteryl oleate. These data indicate that cholesterol derived from cholesterol ester is preferentially absorbed over free cholesterol (FIG. 6a).

Figure 6C:
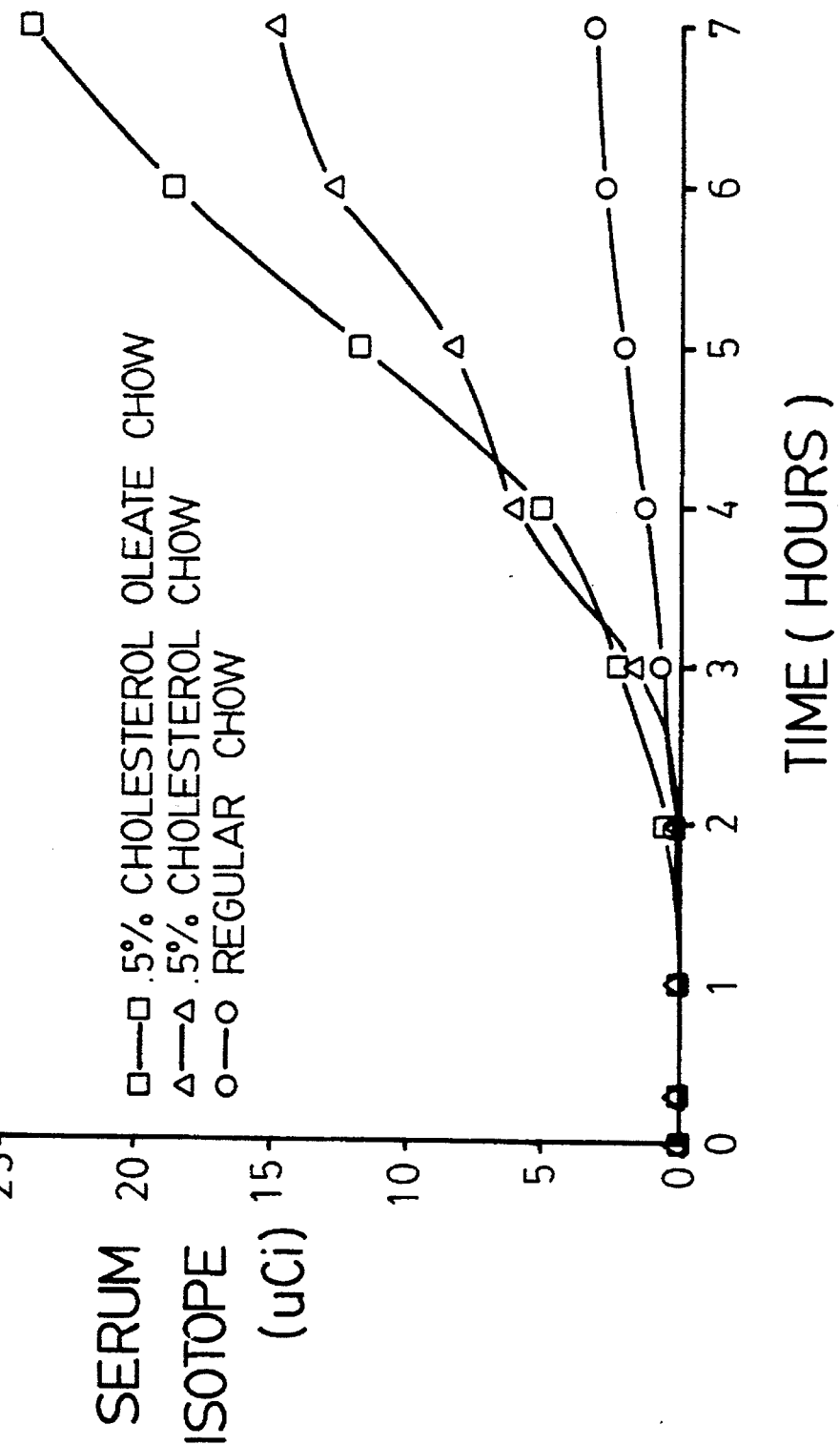
FIG. 6c shows serum recovery of tritiated cholesterol from labeled cholesterol chow and cholesterol.

This preferential absorption was demonstrated in a second way. One rabbit from each of the three groups described above was fasted for twelve hours. A nasogastric tube was inserted into the test rabbit and 10 ml of Tris buffer containing a suspension of 20 uCi of $^3$H-cholesterol incorporated in phosphatidylcholine vesicles were added. This was immediately followed by 10 ml of 20 uCi of $^{14}$C-cholesteryl oleate administered in the same way. Blood was then drawn from an ear vein and 100 µl of plasma was counted for $^{14}$C and $^3$H. As shown, either radiolabeled cholesteryl oleate (FIG. 6b) or radiolabeled cholesterol (FIG. 6c) is preferentially absorbed in rabbits that have been maintained on a cholesteryl oleate diet.

EXAMPLE 11

A New Zealand White rabbit was maintained on regular rabbit chow. Two days before the experiment began the animal was fed chow to which cellulose sulfate had been added to give a final concentration of 0.5%. After 12 hrs. on regular chow then, the experiment began with the administration of $^{14}$C-cholesteryl oleate as described above. The animal was then allowed to eat and drink regular chow in a normal manner. Blood samples were withdrawn from an ear vein and the radiolabeled cholesterol measured by scintillation counting. As shown in FIG. 7, throughout the course of the experiment, the level of serum cholesterol was reduced by 50% in the rabbit fed cellulose sulfate when compared to that of the control rabbit. Moreover, cholesterol did not appear in the serum of the experimental animal until four hours after the administration of the label. In contrast, in the control animal, label appears only two hours after its administration.

EXAMPLE 12

Commercially available bovine pancreatic cholesterol esterase in 10 mM NaCl, 10 mM Tris pH 7.2, was applied to heparin-Sepharose (1.5×10 cm) equilibrated with the same buffer. The resin was developed further by washing with 100 mM Tris, pH 7.2, and little or no activity was found in any of these preliminary steps, even Though virtually all of the applied protein was eluted. When the absorbance at 280 nm returned to zero, the resin was washed with 20 mM sodium taurocholate containing enough sodium chloride to give the same conductivity as that of the previous buffer. All the activity was eluted in several fractions. This single purification step typically provides a 60 to 80% yield with a 50- to 100-fold purification and gives a single band at 67 kDa on SDS-PAGE.

Five hundred micrograms of this homogeneous 67 kDa protein were emulsified in Freund's complete adjuvant and injected subcutaneously into a New Zealand White rabbit. Twenty-one days later the rabbit was boosted with intraperitoneal injections of 250 µg protein dissolved in 1 ml of 10 mM sodium phosphate, 150 mM NaCl, pH 7.1. The rabbits were bled 10 days later, and the presence of anti-cholesterol IgG was determined on Ouchterlony plates.

Bovine 72 kDa cholesterol esterase was assayed in the presence of this antibody. In a typical assay, 75 oleate vesicles, 25 µl of diluted antibody, 25 µl of 100 mM taurocholate, 175 µl of 150 mM Tris, pH 7.5 were mixed in a test tube and hydrolysis was initiated by adding 25 µl of enzyme to the reaction mixture at 37° C. After five minutes, the reaction was quenched by addition of 600 µl of 0.3 NaOH and 3 ml of benzene:methanol:chloroform (1:1.2:0.5). After mixing, the samples were centrifuged and 1 ml of the clear aqueous phase was removed and counted for radioactivity. The control activity was determined in the absence of added antibody. Following this protocol, serum containing antibody to the 67 kDa cholesterol esterase was found to be a potent inhibitor of the bovine 72 kDa enzyme. Thus, diluting the serum $10^5$ times produced 50% inhibition.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for inhibiting the intestinal absorption of cholesterol in a mammal by administering orally a non-absorbable inhibitor of cholesterol esterase comprising a 3-sulfated polysaccharide having a molecular weight greater than 100,000 Da.

2. A method according to claim 1 for inhibiting the intestine absorption of cholesterol comprising orally administering an effective amount of the non-absorbable synthetic 3-sulfated polysaccharide to inhibit pancreatic cholesterol esterase.

3. A method for decreasing cholesterol absorption in mammals comprising orally administering an effective amount of 3-sulfated dextran having a molecular weight greater than 500,000 Da.

4. A method according to claim 1 for inhibiting the intestinal absorption of cholesterol wherein the 3-sulfated non-absorbable polysaccharide is selected from the group consisting of alginic acid, pectin, amylopectin, chitin, dextran, cellulose, agar or chitosan.

5. A food product including a foodstuff and an effective amount of a non-absorbable synthetic 3-sulfated polysaccharide having a molecular weight greater than 100,000 Da.

6. A food product according to claim 5 containing a foodstuff and an effective amount of a non-absorbable 3-sulfated polysaccharide having a molecular weight greater than 100 OVV Da to inhibit pancreatic cholesterol esterase.

7. A food product according to claim 5, wherein the non-absorbable polysaccharide is selected from the group consisting of 3-sulfated alginic acid, pectin, amylopectin, chitin, cellulose, agar or chitosan.

8. A method for decreasing cholesterol absorption in a mammal comprising ingesting the food product of claim 6.

9. A method of decreasing serum cholesterol levels in a mammal comprising administering an effective amount of a synthetic non-absorbable 3-sulfated polysaccharide in combination with an effective amount of Lovastatin.

10. A method of decreasing serum cholesterol levels in mammals comprising administering an effective amount of a synthetic non-absorbable 3-sulfated polysaccharide in combination with an effective amount of triglyceride lipase inhibitor.

11. A method of decreasing serum cholesterol levels in mammals comprising administering an effective amount of a synthetic non-absorbable 3-sulfated polysaccharide in combination with an effective amount of a fatty acyl cholesterol O-acyl transferase inhibitor.

12. A method for decreasing fatty acid absorption in mammals comprising orally administering an effective amount of a 3-sulfated polysaccharide having a molecular weight greater than 100,000 Da selected from the group consisting of cellulose, agar, amylopectin, chitin, chitosan, pectin, and alginic acid.

* * * * *